US011819577B2

(12) United States Patent
Sharma et al.

(10) Patent No.: US 11,819,577 B2
(45) Date of Patent: *Nov. 21, 2023

(54) FIXED DOSE PHARMACEUTICAL COMPOSITION OF VALSARTAN AND SACUBITRIL

(71) Applicant: MANKIND PHARMA LTD, New Delhi (IN)

(72) Inventors: Bharat Sharma, Gurugram (IN); K. S. Hareen, Gurugram (IN); P. V. S Narasimham, Gurugram (IN); Anil Kumar, Gurugram (IN)

(73) Assignee: Mankind Pharma Ltd., New Delhi (IN)

( * ) Notice: Subject to any disclaimer, the term of this patent is extended or adjusted under 35 U.S.C. 154(b) by 0 days.

This patent is subject to a terminal disclaimer.

(21) Appl. No.: 17/834,260

(22) Filed: Jun. 7, 2022

(65) Prior Publication Data

US 2022/0296527 A1 Sep. 22, 2022

Related U.S. Application Data

(63) Continuation of application No. 16/627,157, filed as application No. PCT/IB2018/054842 on Jun. 29, 2018, now Pat. No. 11,382,866.

(30) Foreign Application Priority Data

Jul. 6, 2017 (IN) .............................. 201711023733

(51) Int. Cl.
    *A61K 9/24* (2006.01)
    *A61K 31/165* (2006.01)
    *A61K 31/41* (2006.01)
    *A61K 47/12* (2006.01)

(52) U.S. Cl.
    CPC ............ *A61K 9/209* (2013.01); *A61K 31/165* (2013.01); *A61K 31/41* (2013.01); *A61K 47/12* (2013.01)

(58) Field of Classification Search
    CPC .......... A61P 9/04; A61P 9/12; C07B 2200/07; C07B 2200/13; C07C 231/24; C07C 233/47; C07D 257/04
    See application file for complete search history.

(56) References Cited

U.S. PATENT DOCUMENTS

| 7,468,390 | B2 | 12/2008 | Ksander et al. |
| 8,877,938 | B2 | 11/2014 | Feng et al. |
| 9,517,226 | B2 | 12/2016 | Schumacher et al. |
| 11,382,866 | B2 * | 7/2022 | Sharma .................. A61K 47/12 |
| 2004/0033258 | A1 | 2/2004 | Koike |
| 2010/0003321 | A1 | 1/2010 | Cao et al. |
| 2010/0267786 | A1 | 10/2010 | Al-Fayoumi et al. |
| 2016/0206597 | A1 | 7/2016 | Bransford et al. |

FOREIGN PATENT DOCUMENTS

| CN | 105837464 | 8/2016 |
| EP | 3054925 | 8/2016 |
| WO | 2002/06253 | 1/2002 |
| WO | 2003/059345 | 7/2003 |
| WO | 2009/061713 | 5/2009 |
| WO | 2012/077968 | 6/2012 |
| WO | 2015/028941 | 3/2015 |
| WO | 2016/181284 | 11/2016 |
| WO | 2017/000864 | 1/2017 |
| WO | 2017/009784 | 1/2017 |
| WO | 2017/012600 | 1/2017 |
| WO | 2017/012917 | 1/2017 |
| WO | 2017/020841 | 2/2017 |
| WO | 2017/036420 | 3/2017 |
| WO | 2017/037577 | 3/2017 |
| WO | 2017/042700 | 3/2017 |

OTHER PUBLICATIONS

International Search Report, issued in the corresponding PCT application No. PCT/IB2018/054842, dated Sep. 20, 2018, 5 pages.

* cited by examiner

*Primary Examiner* — Audrea B Coniglio
(74) *Attorney, Agent, or Firm* — Hamre, Schumann, Mueller & Larson, P.C.

(57) ABSTRACT

This present invention relates to pharmaceutical composition comprising fixed dose combination of valsartan or pharmaceutically acceptable salts thereof and sacubitril or pharmaceutically acceptable salts thereof. Further this invention also relates to process for the preparation of said composition and use of the said composition in treatment of certain diseases.

17 Claims, No Drawings

FIXED DOSE PHARMACEUTICAL COMPOSITION OF VALSARTAN AND SACUBITRIL

CROSS-REFERENCE TO RELATED APPLICATIONS

This application is a continuation application of U.S. patent application Ser. No. 16/627,157 filed Dec. 27, 2019, which is a U.S. national stage application under 35 U.S.C. § 371 of PCT Application No. PCT/IB2018/054842, filed Jun. 29, 2018, which claims priority to Indian Patent Application No. 201711023733, filed Jul. 6, 2017, the entireties of which are incorporated herein by reference.

FIELD OF THE INVENTION

The present invention relates to pharmaceutical composition comprising fixed dose combination of sacubitril or pharmaceutically acceptable salts thereof and valsartan or pharmaceutically acceptable salts thereof. Further, this invention also relates to a process for the preparation of said composition and use of said composition in treatment of certain diseases.

BACKGROUND OF THE INVENTION

Heart failure (HF) is a major and increasing clinical problem that is associated with substantial morbidity and mortality. It is the leading cause of admission to hospital in individuals older than 65 years.

Heart failure remains a high unmet medical need with an annual mortality rate of about 20%. Reductions in mortality and cardiovascular morbidity have been achieved by the renin-angiotensin-aldosterone system (RAAS) blockers (Angiotensin converting enzyme (ACE) inhibitors and Angiotensin receptor blockers (ARBs)) and β3 receptor blockers in HF. While survival rates have improved for HF with reduced ejection fraction (HF-REF) over recent decades, due to more widespread use of drugs that block RAAS and improved acute care, residual mortality rates remain high. For patients with HF with preserved ejection fraction (HF-PEF) no therapy has proven to be effective at reducing morbidity and mortality. Overall, the therapeutic benefits of RAAS blockade with ACE inhibitors and/or ARBs remain limited, possibly caused by angiotensin II escape due to incomplete ACE inhibition or angiotensin 11 originating from alternative non-ACE pathways, and by other neuro-hormonal and other mechanisms contributing to cardiac disease and outcomes.

A supramolecular complex comprising valsartan, which is an ARB, and AHU-377 (Sacubitril), which is a neprilysin inhibitor, has been approved by US Food and Drug Administration (FDA) under the brand name Entresto® (LCZ696) for the treatment of heart failure with reduced ejection fraction.

Valsartan blocks the angiotensin II receptor type 1 (ATI). This receptor is found on both vascular smooth muscle cells and the zona glomerulosa cells of the adrenal gland which are responsible for aldosterone secretion. In the absence of ATI blockade, angiotensin causes both direct vasoconstriction and adrenal aldosterone secretion, the aldosterone then acting on the distal tubular cells of the kidney to promote sodium reabsorption which expands extracellular fluid (ECF) volume. Blockade of angiotensin II receptors thus causes vasodilation and reduction of ECF volume.

AHC-377 is a prodrug that is activated to sacubitrilat (LBQ657) by de-ethylation via esterases. AHU-377 inhibits the enzyme neprilysin, a neutral endopeptidase that degrades vasoactive peptides, including natriuretic peptides, bradykinin, and adrenomedullin. Thus, AHU-377 increases the levels of these peptides, causing vasodilation and reduction of ECF volume via sodium excretion.

Entresto® is a first-in-class medicine (Angiotensin Receptor Neprilysin Inhibitor, or AR) and has a unique mode of action which is thought to reduce the strain on the failing heart, it harnesses the body's natural defenses against heart failure, simultaneously acting to enhance the levels of natriuretic and other endogenous vasoactive peptides, while also inhibiting the renin-angiotensin-aldosterone system (AAS).

There are several patent and non-patent literature known in the art which disclose the formulation/pharmaceutical composition/dosages form of valsartan and sacubitril with one or more pharmaceutically acceptable excipients and used in the treatment of various diseases.

U.S. Pat. No. 7,468,390 discloses a combination of sacubitril and valsartan in amount that achieve a greater antihypertensive effect than the sum of the therapeutic effects achievable with the amounts of sacubitril and valsartan administered alone.

U.S. Pat. No. 8,877,938 discloses a crystalline complex of sacubitril and valsartan.

U.S. Pat. No. 9,517,226 discloses a method for the treatment or delay of progression of a disease characterized by atrial enlargement and/or remodeling in a human patient, wherein the disease is heart failure with preserved ejection fraction (HF-PEF).

US Patent Publication No. 20160206597 discloses a method for the protection of the kidney suffering from hypertension or heart failure comprising complex or combination of valsartan & sacubitril.

US Patent Publication No. 20100267786 discloses a dosage form comprising valsartan sacubitril complex in a concentration from about 4% to about 90%.

PCT Patent Publication No. 2017037577 discloses a composition comprising of combination of valsartan and sacubitril in a 1:1 molar ratio for use in reducing arterial stiffness.

PCT Patent Publication No. 2016181284 discloses a regimen for treating heart failure which comprises twice-daily target dose of 200 mg of sacubitril and valsartan in a 1:1 molar ratio.

PCT Patent Publication No. 2017042700 discloses a solid forms comprising valsartan and sacubitril, solid salt forms comprising valsartan and sacubitril and amorphous solid salt form comprising sacubitril and valsartan.

PCT Patent Publication No. 2017036420 discloses a composition containing sacubitril and valsartan in amorphous form.

PCT Patent Publication No. 2017020841 discloses a pharmaceutical composition containing a specific crystalline powder of valsartan-sacubitril complex having 20 μm≤D 90≤100 μm.

PCT Patent Publication No. 2017012917 discloses an amorphous solid dispersion comprising a 1:1 stoichiometric mixture of sodium salts of Valsartan and Sacubitril.

PCT Patent Publication No. 2017012600 discloses a composition containing valsartan, and sacubitril with excipients.

PCT Patent Publication No. 2017009784 discloses Form II, III, IV and amorphous form of tri-sodium salt of valsartan sacubitril complex and covers crystalline form of sacubitril sodium.

PCT Patent Publication No. 2017000864 discloses a composition comprising LCZ696, a hydrophilic filler, a binder and a disintegrant There is an unmet need for providing an alternate fixed dose pharmaceutical composition comprising a combination of valsartan and sacubitril, which is bioequivalent to the marketed pharmaceutical composition comprising valsartan and sacubitril as crystalline supramolecular complex.

SUMMARY OF THE INVENTION

The present invention provides a pharmaceutical composition of valsartan and sacubitril and one or more pharmaceutically acceptable excipients and process of preparation thereof.

An aspect of the present invention provides a pharmaceutical composition comprising:
(1) a first component which comprises:
(a) first portion, wherein said first portion comprises sacubitril or its pharmaceutically acceptable salts, with one or more pharmaceutically acceptable excipients;
(b) optionally second portion, wherein said second portion comprises one or more pharmaceutically acceptable excipients; and
(2) a second component which comprises:
(a) first portion, wherein said first portion comprises valsartan or its pharmaceutically acceptable salts, with one or more pharmaceutically acceptable excipients;
(b) optionally second portion, wherein said second portion comprises one or more pharmaceutically acceptable excipients; wherein the weight ratio of the first component to the second component is about 1:2 to about 2:1.

One embodiment of the present invention provides a pharmaceutical composition, wherein valsartan is present in form of disodium salt.

Another embodiment of the present invention provides a pharmaceutical composition, wherein valsartan is present in amorphous or crystalline form.

Another embodiment of the present invention provides a pharmaceutical composition, wherein sacubitril is present in form of monosodium salt.

According to another embodiment of the present invention, sacubitril is present in amorphous or crystalline form.

According to another embodiment of the present invention, the first or second component is present in the form of powder, slugs, compacts, granules, beads, pellets, or minitablets.

According to another embodiment, the present invention provides a pharmaceutical composition which is in the form of tablet.

According to another embodiment of the present invention, the first and second components are present in a single layer or in separate layers.

According to another embodiment, the present invention provides a pharmaceutical composition comprising valsartan and sacubitril and one or more pharmaceutically acceptable excipients, wherein said composition is a mono-layer tablet.

According to yet another preferred embodiment, the present invention provides a pharmaceutical composition which is in the form of bilayer tablet.

According to another embodiment, the pharmaceutical composition is further film coated.

According to another embodiment, the film coating comprises film forming polymer and one or more pharmaceutically acceptable excipients.

According to another embodiment, the film coating comprises magnesium stearate.

According to another embodiment of the present invention, the total weight of first component is about 100 mg to about 400 mg.

According to another embodiment of the present invention, the total weight of second component is about 100 mg to about 400 mg.

According to another embodiment of the present invention, the total weight of pharmaceutical composition is about 300 mg to about 600 mg.

Another embodiment of the present invention provides a method for the treatment of heart failure in a patient comprising administering to the patient a pharmaceutical composition comprising:
(1) a first component which comprises:
(a) first portion, wherein said first portion comprises sacubitril or its pharmaceutically acceptable salts, with one or more pharmaceutically acceptable excipients;
(b) optionally second portion, wherein said second portion comprises one or more pharmaceutically acceptable excipients; and
(2) a second component which comprises:
(a) first portion, wherein said first portion comprises valsartan or its pharmaceutically acceptable salts, with one or more pharmaceutically acceptable excipients;
(b) optionally second portion, wherein said second portion comprises one or more pharmaceutically acceptable excipients; wherein the weight ratio of the first component to the second component is about 1:2 to about 2:1.

Another embodiment of the present invention provides a pharmaceutical composition which is prepared by the process of dry granulation or direct compression.

According to another embodiment of the present invention, the pharmaceutical composition of the present invention is formed with a compression force between 2 to 30 kN.

According to another embodiment of the present invention, the pharmaceutical composition of the present invention has hardness between 8 kp to 15 kp.

According to yet another embodiment of the present invention, the pharmaceutically acceptable excipients are selected from the group comprising of one or more of filler/diluent, binder, disintegrant, lubricant, plasticizer, pH adjusting agent, pigment, opacifier, surfactant, glidant and/or combinations thereof.

Another aspect of the present invention provides a process for preparing a pharmaceutical composition wherein said process comprises the steps of: (a) preparing a mix of valsartan and sacubitril and one or more pharmaceutically acceptable excipients; (b) lubricating the mixture of step (a) with lubricants; (c) granulating the mixture obtain in step (b); (d) lubricating the mixture of step (c) with lubricants; (e) formulating the lubricated granules of step (d) to form final dosage form.

Another embodiment of the present invention provides a process for preparing the pharmaceutical composition, wherein said process is performed in an environment of equal or less than 35% relative humidity.

The details of one or more embodiments of the inventions are set forth in the description below. Other features, objects and advantages of the inventions will be apparent from the description and claims.

DESCRIPTION OF THE INVENTION

The present invention relates to fixed dose pharmaceutical compositions comprising therapeutic effective amount of valsartan or a pharmaceutically acceptable salt thereof and sacubitril or a pharmaceutically acceptable salt thereof and process for their preparation.

The present invention provides a pharmaceutical composition comprising:
(1) a first component which comprises:
(a) first portion, wherein said first portion comprises sacubitril or its pharmaceutically acceptable salts, with one or more pharmaceutically acceptable excipients;
(a) optionally second portion, wherein said second portion comprises one or more pharmaceutically acceptable excipients; and
(2) a second component which comprises:
(a) first portion, wherein said first portion comprises valsartan or its pharmaceutically acceptable salts, with one or more pharmaceutically acceptable excipients;
(b) optionally second portion, wherein said second portion comprises one or more pharmaceutically acceptable excipients; wherein the weight ratio of the first component to the second component is about 1:2 to about 2:1.

The present invention provides a pharmaceutical composition comprising (i) sacubitril or a pharmaceutically acceptable salt thereof; and (ii) valsartan or pharmaceutically acceptable salts thereof, wherein the amounts of sacubitril and valsartan thereof when administered in combination achieve a greater therapeutic effect than the sum of the therapeutic effects achievable with the amounts of sacubitril and valsartan thereof when administered alone.

The term "therapeutically effective amount" or "effective amount" used interchangeably, is defined to mean the amount or quantity of the active drug, which is sufficient to elicit an appreciable biological response when administered to the patient. It will be appreciated that the precise therapeutic dose will depend on the age and condition of the patient, nature of the condition to be treated and will be at the ultimate discretion of the attendant physician.

As used herein, "fixed dose combination" refers to a combination of defined doses of two drugs or active ingredients presented in a single dosage unit (e.g. a tablet or a capsule) and administered as such.

The term "valsartan", as used herein, may include free acid forms of valsartan and its pharmaceutically acceptable and therapeutically active salts, esters, amides, prodrugs, metabolites, enantiomers, polymorphs, analogues, etc. that induce a desired pharmacological or physiological effect.

The term "sacubitril", as used herein, as used herein, may include free acid forms of valsartan and its pharmaceutically acceptable and therapeutically active salts, esters, amides, prodrugs, metabolites, enantiomers, polymorphs, analogues, etc. that induce a desired pharmacological or physiological effect.

In present invention, the terms like "active", "active agent", "active substance" or "active ingredient" may be used synonymously for "sacubitril" or "valsartan".

The term "stable or stability or stabilized" means the dosages form are stable under accelerated conditions (40° C./75% RH) and also under normal conditions (25° C./60% RH).

As used in this specification and the appended claims, the singular forms "a", "an", and "the" include plural references unless the context clearly dictates otherwise. Thus for example, a reference to "a method" or "a process" includes one or more methods, one or more processes and/or steps of the type described herein and/or which will become apparent to those persons skilled in the art upon reading this disclosure and so forth.

The present invention provides a solid dosage form comprising a pharmaceutical composition of disodium salt of valsartan and mono sodium salt of sacubitril and one or more pharmaceutically acceptable excipient.

The present invention provides a pharmaceutical composition of valsartan and sacubitril, wherein the valsartan or a pharmaceutically acceptable salt thereof is present in an amount of about 1 mg to 200 mg.

The present invention provides a pharmaceutical composition of valsartan and sacubitril, wherein the sacubitril or a pharmaceutically acceptable salt thereof is present in an amount of about 1 mg to 200 mg.

The present invention provides a pharmaceutical composition of valsartan and sacubitril, wherein the valsartan having a particle size of d90 in the range of 1-300 microns.

The present invention provides a pharmaceutical composition of valsartan and sacubitril, wherein the sacubitril having a particle size of d90 in the range of 1-300 microns.

The present invention provides a pharmaceutical composition of sacubitril and valsartan, wherein the valsartan or sacubitril may be present in the form of crystalline or amorphous or solvates or hydrates thereof.

The present invention provides a pharmaceutical composition of sacubitril and valsartan comprising first and second component, wherein the first and the second components are present as a single entity or as separate entities.

The present invention provides a pharmaceutical composition comprising valsartan and sacubitril and one or more pharmaceutically acceptable excipients, wherein said composition is a mono-layer tablet.

The present invention provides a pharmaceutical composition of sacubitril and valsartan comprising first and second component, wherein the first component is physically separated from the second component.

The present invention provides a pharmaceutical composition of sacubitril and valsartan comprising first and second component, wherein the first component is separated from the second component by an intermediate, inactive layer.

The present invention provides a pharmaceutical composition of sacubitril and valsartan comprising first and second component, wherein the first and the second components are administered in one unit dosage form or in two separate unit dosage forms.

The present invention provides a pharmaceutical composition of sacubitril and valsartan, wherein the composition is free from supramolecular complex of sacubitril and valsartan.

The weight ratio of the first component to the second component is about 1:2 to about 2:1. The total weight of first component is about 100 mg to about 400 mg. The total weight of second component is about 100 mg to about 400 mg.

The first component and second component of the present invention is in the form of powder, slugs, compacts, granules, granulate, grains, beads, pellets, or minitablets. The first and second component of the present invention may be further coated.

The term "composition" or "dosage form" or "pharmaceutical composition" as used herein synonymously include tablet such as mono-layered/single layer tablets, bilayered tablets, trilayered tablet, multilayer tablet, drug layered tablet, caplets, minitablets, capsules, tablet in tablet, tablets in a capsule, granules in a capsule, pellets, pellets in a capsule, beads, powder, granules, sachets, suspension or any other suitable dosage form meant for oral administration.

The pharmaceutical composition is further coated with a protective or film coating. More preferably, the pharmaceutical composition is a bilayer tablet. The total weight of pharmaceutical composition is about 300 mg to about 600 mg.

The pharmaceutical composition of the present invention can be prepared by any suitable method known in the art such as direct compression, dry or wet granulation, fluidized bed granulation, melt extrusion, melt granulation, hot melt granulation, extrusion granulation, spray coating, freeze drying, spray drying and solution evaporation.

In some embodiments, the oral pharmaceutical composition of the present invention is further film coated using techniques well known in the art, such as spray coating in a conventional coating pan or dip coating. The film coating comprises film forming polymers and one or more pharmaceutically acceptable excipients.

Suitable film forming polymers are selected from the group comprising cellulose derivatives, e.g., methyl cellulose, hydroxymethyl cellulose, hydroxyethyl cellulose, hydroxypropyl cellulose, hydroxymethylethyl cellulose, hydroxypropylmethyl cellulose, sodium carboxymethyl cellulose, and ethyl cellulose; vinyl polymers, e.g., polyvinylpyrrolidones; acrylic polymers; and mixtures thereof. Alternatively, commercially available coating compositions comprising film forming polymers marketed under various trade names, e.g., Opadry®, may be used for coating along with other pharmaceutically acceptable excipients such as magnesium stearate.

Examples of solvents used for preparing the coating solution are selected from purified water, methyl alcohol, ethyl alcohol, isopropyl alcohol, n-butyl alcohol, acetone, acetonitrile, chloroform, methylene chloride, and mixtures thereof.

In some embodiments, the film-coating provides for immediate release, extended release, sustained release, delayed release, enteric release, or intestinal release of the active agent.

The pharmaceutical composition of the present invention is used in the treatment or prevention of a condition or disease selected from the group consisting of hypertension, heart failure, such as (acute and chronic) congestive heart failure, left ventricular dysfunction and hypertrophic cardiomyopathy, diabetic cardiac myopathy, supraventricular and ventricular arrhythmias, atrial fibrillation, atrial flutter, detrimental vascular remodeling, myocardial infarction and its sequelae, atherosclerosis, angina (whether unstable or stable), renal insufficiency (diabetic and non-diabetic), heart failure, angina pectoris, diabetes, secondary aldosteronism, primary and secondary pulmonary hypertension, renal failure conditions, such as diabetic nephropathy, glomerulonephritis, scleroderma, glomerular sclerosis, proteinuria of primary renal disease, and also renal vascular hypertension, diabetic retinopathy, the management of other vascular disorders, such as migraine, peripheral vascular disease, Raynaud's disease, luminal hyperplasia, cognitive dysfunction, such as Alzheimer's, glaucoma and stroke.

The pharmaceutically acceptable excipients of the present invention may include filler, binder, disintegrant, lubricant, diluent, plasticizer, pH adjusting agent, pigment, opacifier, surfactant, glidant, and/or any combinations thereof. Some of the excipients may have two or more functions at the same time.

Suitable fillers/diluents include, without limitation, starch, corn starch, potato starch, pregelatinized starch, dry starch, disaccharides, lactose, cellulose, cellulose derivatives, such as silicified microcrystalline cellulose, microcrystalline cellulose (e.g., cellulose MK GR), mannitol, sorbitol, xylitol, trehalose, colloidal silica, sucrose or other sugars or sugar derivatives, calcium hydrogen phosphate, dicalcium phosphate, and combinations thereof. When present, a filler may be employed in an amount ranging from about 10% to about 80%, preferably from about 20% to about 70% by weight of the tablet (prior to any optional film coating).

Suitable binders include, without limitation, microcrystalline cellulose, polyvinylpyrrolidone (PVP), such as e.g., PVP K 30 or PVP90F, polyethylene glycols (PEG), e.g., PEG 4000, hydroxypropylmethyl cellulose, hydroxypropyl cellulose, both preferably of medium to high viscosity, e.g. viscosity grades 3 or 6 cps, pregelatinized starch and combinations thereof. When present, a binder may be employed in an amount ranging from about 0.1% to about 20%, preferably from about 0.5% to about 15%, such as 0.7% to 5%, by weight of the tablet (prior to any optional film coating).

Suitable lubricants include, without limitation, zinc stearate, magnesium stearate, aluminum or calcium silicate, stearic acid, PEG 4000-8000, talc and combinations thereof. When present, a lubricant may be employed in an amount ranging from about 0.01% to about 10%, preferably from about 0.1% to about 5%, by weight of the tablet (prior to any optional film coating).

Suitable disintegrants include, without limitation, carboxymethylcellulose calcium (CMC-Ca), carboxymethylcellulose sodium (CMC-Na), crosslinked PVP (e.g. crospovidone, polyplasdone or kollidon XL), croscarmellose sodium, alginic acid, sodium alginate and guar gum, most preferably crosslinked PVP (crospovidone), crosslinked CMC (Ac-Di-Sol), carboxymethyl starch-Na (pirimojel and explotab). A disintegrant is employed in an amount of 0.01 to 15%, such as of 0.05 to 12%, such as at least 0.1 to 10%, by weight of the tablet, said percentage of weight being defined prior to any optional film coating. In particular, the disintegrant is crospovidone.

Suitable glidants include, without limitation, zinc stearate, colloidal silicon dioxide (e.g., Aerosil 200), magnesium trisilicate, powdered cellulose, starch, talc and combinations thereof. When present, a glidant may be employed in an amount ranging from about 0.01% to about 10%, preferably from about 0.1% to about 5%, by weight of the tablet (prior to any optional film coating).

The surfactants include but are not limited to anionic, cationic, non-ionic or amphoteric surfactants or those known to the person skilled in the art. Further, the amount of surfactant present in the dosages form of valsartan and sacubitril, or salt thereof ranges from about 0.1% to about 5% by total weight of the composition.

Suitable pH adjusting agents are selected form the group comprising meglumine, Na2HP04, Mg(OH)2, sodium hydroxide, carbonates, potassium citrate, sodium citrate and other pharmaceutically acceptable alkalizing salts.

Suitable plasticizers are selected from the group comprising triethylcitrate, dibutyl sebacate, acetylated triacetin, tributylcitrate, glycerotributyrate, monoglyceride, rapeseed oil, olive oil, sesame oil, acetyltributylcitrate, acetyltriethylcitrate, glycerin, sorbitol, diethyl oxalate, diethyl phthalate, diethyl malate, diethyl fumarate, dibutyl succinate, diethyl malonate, dioctyl phthalate, or mixtures thereof.

Suitable opacifiers are selected from the group comprising titanium dioxide, manganese dioxide, iron oxide, silicon dioxide, or mixtures thereof.

Suitable colorants include natural colorants i.e., pigments and dyes obtained from mineral, plant, and animal sources. Examples of natural colorants include red ferric oxide, yellow ferric oxide, ferrosoferric oxide, alizarin, indigo, rutin, quercetin, and the like. Synthetic colorants may also be used, which is typically an FD&C or D&C dye, e.g., an approved dye selected from the so-called 'coal-tar' dyes, such as a nitroso dye, a nitro dye, an azo dye, an oxazine, a thiazine, a pyrazolone, a xanthene, an indigoid, an anthraquinone, an acridine, a rosaniline, a phthalein, a quinoline, or a 'lake' thereof, i.e. an aluminum or calcium salt thereof. Particularly preferred colorants are food colorants in the 'GRAS' (Generally Regarded as Safe) category.

The present invention provides a process for preparing a pharmaceutical composition wherein said process comprises the steps of: (a) preparing a mix of valsartan and sacubitril and one or more pharmaceutically acceptable excipients; (b) lubricating the mixture of step (a) with lubricants; (c) granulating the mixture obtain in step (b); (d) lubricating the mixture of step (c) with lubricants; (e) formulating the lubricated granules of step (d) to form final dosage form.

The present invention provides a process for preparing a pharmaceutical composition wherein said process comprises the steps of: (a) preparing a mix of sacubitril and one or more pharmaceutically acceptable excipients; (b) lubricating the mixture of step (a) with lubricants; (c) granulating the mixture obtained in step (b) to form granules; (d) blending and lubricating the granules of step (c); (e) preparing a mix of one or more pharmaceutically acceptable excipients; (f) granulating the mixture obtain in step (e) to form granules; (g) mixing the granules of step (d) and step (f) to form a final blend for first component; (h) preparing a mix of valsartan and one or more pharmaceutically acceptable excipients; (i) lubricating the mixture of step (h) with lubricants; (j) granulating the mixture obtained in step (i) to form granules; (k) lubricating the granules obtained in step (j); (l) preparing a mix of one or more pharmaceutically acceptable excipients; (m) granulating the mixture obtain in step (l) to form granules; (n) mixing the granules obtained in step (k) with granules of step (m) and then lubricated to form final blend for second component; (o) converting the final blends obtained in step (g) and (m) into final dosage form.

Preferably, the process for the preparation of the pharmaceutical composition of the present invention is performed in an environment of a relative humidity equal or less than 30%.

The pharmaceutical composition of the present invention is formed with a compression force ranging from 2 to 30 kN.

The pharmaceutical composition of the present invention should have a suitable hardness, i.e., an average hardness ranging from 5 kp to 30 kp, preferably between 8 kp to 15 kp.

The invention is further illustrated by the following examples which are provided to be exemplary of the invention and do not limit the scope of the invention. While the present invention has been described in terms of its specific embodiments, certain modifications and equivalents will be apparent to those skilled in the art and are intended to be included within the scope of the present invention.

Example 1

| S. No. | Ingredient | Qty./Tablet (% w/w) |
|---|---|---|
| 1 | Sacubitril | 10-40 |
| 2 | Valsartan | 10-40 |
| 3 | Microcrystalline cellulose | 20-70 |
| 4 | Croscarmellose sodium | 0.1-10 |
| 5 | Colloidal Silicon dioxide | 0.1-5 |

-continued

| S. No. | Ingredient | Qty./Tablet (% w/w) |
|---|---|---|
| 6 | Zinc stearate | 0.1-5 |
| Film Coating | | |
| 7 | Opadry white | 0.5-7.5 |
| 8 | Isopropyl alcohol | q.s. |
| 9 | Methylene chloride | q.s. |

Manufacturing Procedure: Sacubitril, valsartan and one or more pharmaceutically acceptable excipients were mixed in blender to form uniform mixture. To this mixture lubricant was added and mixed uniformly. The mixture was dry granulated using roller compactor and ribbons were milled and sifted. The granules thus obtained were blended with lubricant and the resulting blend was formulated into suitable dosage form.

Example 2

| S. No. | Ingredient | Qty./Tablet (mg) |
|---|---|---|
| First component | | |
| 1 | Sacubitril | 97.0 |
| 2 | Microcrystalline cellulose | 89.0 |
| 3 | Croscarmellose sodium | 10.0 |
| 4 | Colloidal Silicon dioxide | 2.0 |
| 5 | Zinc stearate | 2.0 |
| Second component | | |
| 6 | Valsartan | 103.0 |
| 7 | Microcrystalline cellulose | 83.0 |
| 8 | Croscarmellose sodium | 10.0 |
| 9 | Colloidal Silicon dioxide | 2.0 |
| 10 | Zinc stearate | 2.0 |
| Film Coating | | |
| 11 | Opadry white | 15.0 |
| 12 | Isopropyl alcohol | q.s |
| 13 | Methylene chloride | q.s |

Manufacturing Procedure:

(i) First Component Preparation Method:

Sacubitril and one or more pharmaceutically acceptable excipients were mixed in blender of form uniform mixture. To this mixture lubricant was added and mixed uniformly. The mixture was dry granulated using roller compactor and ribbons were milled and sifted. The granules thus obtained were blended with lubricant.

(ii) Second Component Preparation Method:

Valsartan and one or more pharmaceutically acceptable excipients were mixed in blender of form uniform mixture. To this mixture lubricant was added and mixed uniformly. The mixture was dry granulated using roller compactor and ribbons were milled and sifted. The granules thus obtained were blended with lubricant.

(iii) Compression of (i) and (ii) layer to form bilayer tablet and film coated the tablet to form final bilayer tablet dosage form.

Example 3

| S. No. | Ingredient | Qty/Tab. (mg) | | |
|---|---|---|---|---|
| | | 97/103 | 49/51 | 24/26 |
| | Sacubitril Layer | | | |
| 1 | Sacubitril Sodium eq. to Sacubitril | 97.200 | 48.600 | 24.300 |
| 2 | Microcrystalline Cellulose | 59.746 | 29.873 | 14.936 |
| 3 | Croscarmellose Sodium | 9.000 | 4.500 | 2.250 |
| 4 | Colloidal Silicon Dioxide | 2.000 | 1.000 | 0.500 |
| 5 | Opadry Lake blend Green | 0.054 | 0.027 | 0.014 |
| | Lubrication before compaction | | | |
| 6 | Magnesium Stearate | 1.000 | 0.500 | 0.250 |
| | Lubrication after compaction | | | |
| 7 | Microcrystalline Cellulose | 10.000 | 5.000 | 2.500 |
| 8 | Magnesium Stearate | 1.000 | 0.500 | 0.250 |
| | Total weight of Sacubitril layer | 180.000 | 90.000 | 45.000 |
| | Valsartan Layer Portion A | | | |
| 9 | Valsartan Disodium eq. to Valsartan | 102.800 | 51.400 | 25.700 |
| 10 | Microcrystalline Cellulose | 36.200 | 18.100 | 9.050 |
| 11 | Croscarmellose Sodium | 7.500 | 3.750 | 1.875 |
| 12 | Colloidal Silicon Dioxide | 1.500 | 0.750 | 0.375 |
| | Lubrication before compaction | | | |
| 13 | Magnesium Stearate | 1.000 | 0.500 | 0.250 |
| | Lubrication after compaction | | | |
| 14 | Magnesium Stearate | 1.000 | 0.500 | 0.250 |
| | Total weight of Portion A | 150.000 | 75.000 | 37.500 |
| | Portion B | | | |
| 15 | Microcrystalline Cellulose | 98.000 | 49.000 | 24.500 |
| 16 | Croscarmellose Sodium | 11.000 | 5.500 | 2.750 |
| 17 | Magnesium Stearate | 1.000 | 0.500 | 0.250 |
| | Total weight of Portion B | 110.000 | 55.000 | 27.500 |
| | Total weight Valsartan Layer(A + B) | 260.000 | 130.000 | 65.000 |
| | Total weight of Core Tablet (Valsartan Layer + Sacubitril Layer) | 440.000 | 220.000 | 110.000 |
| | Film Coating | | | |
| 18 | Opadry | 13.200 | — | — |
| 19 | Opadry | — | 6.600 | — |
| 20 | Opadry | — | — | 3.300 |
| 21 | Methylene Chloride | q.s. | q.s. | q.s. |
| 22 | Isopropyl Alcohol | q.s. | q.s. | q.s. |
| | Total weight of coated tablet | 453.200 | 226.600 | 113.300 |

Brief Manufacturing Process
Sacubitril Layer
1. The pre-sifted sacubitril sodium, microcrystalline cellulose, croscarmellose sodium and colloidal silicon dioxide were mixed in a suitable blender.
2. The dry mixed ingredients of step 1 were lubricated in the blender with magnesium stearate to form blend.
3. The blend obtained in step 2 was passed through roller compactor to obtain compact mass/ribbons which were then milled and passed through the appropriate sieve to obtain granules.
4. Microcrystalline cellulose was added extra granularly to granules of step 3.
5. The material of step 4 was lubricated with magnesium stearate in a suitable blender to form a blend.

Valsartan Layer
(Portion A)
6. The pre-sifted valsartan sodium, microcrystalline cellulose, croscarmellose sodium and colloidal silicon dioxide were mixed in a suitable blender.
7. The dry mixed ingredients of step 6 were lubricated with magnesium stearate to form blend.
8. The blend obtained in step 7 was passed through roller compactor to obtain compact mass/ribbons which were then milled and passed through the appropriate sieve to obtain granules.
9. The granules of step 8 were lubricated with magnesium stearate.

Portion B
10. The pre-sifted materials of portion B were mixed in a suitable blender to form a blend.
11. The blend was passed through roller compactor to obtain compact mass/ribbons which were then milled and passed through the appropriate sieve to obtain granules.
12. The granules of step 9 and 11 were mixed to form a blend.
13. The blends of step 5 and 12 were compressed using suitable tooling on bilayer compression machine to form a bilayer tablet.
14. The bilayer tablet of step 13 was film coated using Opadry.

Example 4

| S. No. | Ingredient | Qty/Tab. (mg) | | |
|---|---|---|---|---|
| | | 97/103 | 49/51 | 24/26 |
| | Sacubitril Layer | | | |
| 1 | Sacubitril Sodium eq. to Sacubitril | 97.200 | 48.600 | 24.300 |
| 2 | Microcrystalline Cellulose | 59.746 | 29.873 | 14.936 |
| 3 | Croscarmellose Sodium | 9.000 | 4.500 | 2.250 |
| 4 | Colloidal Silicon Dioxide | 2.000 | 1.000 | 0.500 |
| 5 | Opadry Lake blend Green | 0.054 | 0.027 | 0.014 |
| | Lubrication before compaction | | | |
| 6 | Magnesium Stearate | 1.000 | 0.500 | 0.250 |
| | Lubrication after compaction | | | |
| 7 | Microcrystalline Cellulose | 10.000 | 5.000 | 2.500 |
| 8 | Magnesium Stearate | 1.000 | 0.500 | 0.250 |
| | Total weight of Sacubitril layer | 180.000 | 90.000 | 45.000 |
| | Valsartan Layer Portion A | | | |
| 9 | Valsartan Disodium eq. to Valsartan | 102.800 | 51.400 | 25.700 |
| 10 | Microcrystalline Cellulose | 36.200 | 18.100 | 9.050 |
| 11 | Croscarmellose Sodium | 7.500 | 3.750 | 1.875 |
| 12 | Colloidal Silicon Dioxide | 1.500 | 0.750 | 0.375 |
| | Lubrication before compaction | | | |
| 13 | Magnesium Stearate | 1.000 | 0.500 | 0.250 |
| | Lubrication after compaction | | | |
| 14 | Magnesium Stearate | 1.000 | 0.500 | 0.250 |
| | Total weight of Portion A | 150.000 | 75.000 | 37.500 |
| | Portion B | | | |
| 15 | Microcrystalline Cellulose | 70.950 | 35.475 | 17.738 |
| 16 | Pregelatinized Starch | 33.000 | 16.500 | 8.250 |
| 17 | Colloidal Silicon Dioxide | 5.500 | 2.750 | 1.375 |
| 18 | Magnesium Stearate | 0.500 | 0.250 | 0.125 |

-continued

| S. No. | Ingredient | Qty/Tab. (mg) 97/103 | 49/51 | 24/26 |
|---|---|---|---|---|
| | Total weight of Portion B | 110.000 | 55.000 | 27.500 |
| | Total weight Valsartan Layer(A + B) | 260.000 | 130.000 | 65.000 |
| | Total weight of Core Tablet (Valsartan Layer + Sacubitril Layer) | 440.000 | 220.000 | 110.000 |
| | Film Coating | | | |
| 19 | Opadry | 13.200 | — | — |
| 20 | Opadry | — | 6.600 | — |
| 21 | Opadry | — | — | 3.300 |
| 22 | Isopropyl Alcohol | q.s. | q.s. | q.s. |
| 23 | Methylene Chloride | q.s. | q.s. | q.s. |
| | Total weight of coated tablet | 453.200 | 226.600 | 113.300 |

The composition of Example 4 can be prepared by the same process as given above for Example 3.

Example 5

| S. No. | Ingredient | Qty/Tab. (mg) 97/103 | 49/51 | 24/26 |
|---|---|---|---|---|
| | Dry Mix | | | |
| 1 | Sacubitril; Valsartan | 220.462 | 110.231 | 55.116 |
| 2 | Microcrystalline Cellulose | 167.538 | 83.769 | 41.884 |
| 3 | Croscarmellose Sodium | 13.200 | 6.600 | 3.300 |
| 4 | Colloidal Silicon Dioxide | 4.400 | 2.200 | 1.100 |
| 5 | Polyvinylpyrollidone | 10.000 | 5.000 | 2.500 |
| | PreLubrication before compaction | | | |
| 6 | Magnesium Stearate | 2.200 | 1.100 | 0.550 |
| | Lubrication after compaction | | | |
| 7 | Microcrystalline Cellulose | 20.000 | 10.000 | 5.000 |
| 8 | Magnesium Stearate | 2.200 | 1.100 | 0.550 |
| | Total weight of core tablet (mg) | 440.000 | 220.000 | 110.000 |
| | Film Coating | | | |
| 9 | Opadry | 13.200 | — | — |
| 10 | Opadry | — | 6.600 | — |
| 11 | Opadry | — | — | |
| 12 | Methylene Chloride | q.s. | q.s. | q.s. |
| 13 | Isopropyl Alcohol | q.s. | q.s. | q.s. |
| | Total weight of coated tablet (mg) | 453.200 | 226.600 | 113.300 |

Brief Manufacturing Process
1. The pre-sifted sacubitril, valsartan, microcrystalline cellulose, polyvinylpyrollidone, croscarmellose sodium and colloidal silicon dioxide were mixed in a suitable blender.
2. The dry mixed ingredients of step 1 were lubricated in the blender with magnesium stearate to form a blend.
3. The blend obtained in step 2 was passed through roller compactor to obtain compact mass/ribbons which were then milled and passed through the appropriate sieve to obtain granules.
4. Granules of step 3 were blended with microcrystalline cellulose, and then further lubricated using magnesium stearate to form blend.
5. The blend of step 4 was compressed to form tablet, which is further film coated using Opadry.

Example 6

| S. No. | Ingredient | Qty/Tab. (mg) 97/103 | 49/51 | 24/26 |
|---|---|---|---|---|
| | Dry Mix | | | |
| 1 | Sacubitril; Valsartan | 220.462 | 110.231 | 55.116 |
| 2 | Microcrystalline Cellulose | 177.538 | 88.769 | 44.384 |
| 3 | Croscarmellose Sodium | 13.200 | 6.600 | 3.300 |
| 4 | Colloidal Silicon Dioxide | 4.400 | 2.200 | 1.100 |
| | PreLubrication before compaction | | | |
| 6 | Magnesium Stearate | 2.200 | 1.100 | 0.550 |
| | Lubrication after compaction | | | |
| 7 | Microcrystalline Cellulose | 20.000 | 10.000 | 5.000 |
| 8 | Magnesium Stearate | 2.200 | 1.100 | 0.550 |
| | Total weight of core tablet (mg) | 440.000 | 220.000 | 110.000 |
| | Film Coating | | | |
| 9 | Opadry | 13.200 | — | — |
| 10 | Opadry | — | 6.600 | — |
| 11 | Opadry | — | — | |
| 12 | Methylene Chloride | q.s. | q.s. | q.s. |
| 13 | Isopropyl Alcohol | q.s. | q.s. | q.s. |
| | Total weight of coated tablet (mg) | 453.200 | 226.600 | 113.300 |

Brief Manufacturing Process
1. The pre-sifted sacubitril, valsartan, microcrystalline cellulose, croscarmellose sodium and colloidal silicon dioxide were mixed in a suitable blender.
2. The dry mixed ingredients of step 1 were lubricated in the blender with magnesium stearate to form a blend.
3. The blend obtained in step 2 was passed through roller compactor to obtain compact mass/ribbons which were then milled and passed through the appropriate sieve to obtain granules.
4. Granules of step 3 were blended with microcrystalline cellulose, and then further lubricated using magnesium stearate to form blend.
5. The blend of step 4 was compressed to form tablet, which is further film coated using non aqueous Opadry coating.

Example 7

| S. No. | Ingredient | Qty/Tab. (mg) 97/103 | 49/51 | 24/26 |
|---|---|---|---|---|
| | Sacubitril Layer | | | |
| 1 | Sacubitril sodium eq. to Sacubitril | 97.200 | 48.600 | 24.300 |
| 2 | Microcrystalline cellulose | 59.746 | 29.873 | 14.936 |
| 3 | Croscarmellose sodium | 9.000 | 4.500 | 2.250 |
| 4 | Colloidal silicon dioxide | 2.000 | 1.000 | 0.500 |
| 5 | Opadry Lake blend Green | 0.054 | 0.027 | 0.014 |
| | Lubrication before compaction | | | |
| 6 | Magnesium stearate | 1.000 | 0.500 | 0.250 |
| | Lubrication after compaction | | | |
| 7 | Croscarmellose sodium | 9.000 | 4.500 | 2.250 |
| 8 | Microcrystalline cellulose | 19.000 | 9.500 | 4.750 |
| 9 | Magnesium stearate | 3.000 | 1.500 | 0.750 |
| | Total weight of Sacubitril layer | 200.000 | 100.000 | 50.000 |

-continued

| S. No. | Ingredient | Qty/Tab. (mg) | | |
|---|---|---|---|---|
| | | 97/103 | 49/51 | 24/26 |
| | Valsartan Layer Portion A | | | |
| 9 | Valsartan disodium eq. to Valsartan | 102.800 | 51.400 | 25.700 |
| 10 | Microcrystalline cellulose | 36.200 | 18.100 | 9.050 |
| 11 | Croscarmellose sodium | 7.500 | 3.750 | 1.875 |
| 12 | Colloidal silicon dioxide | 1.500 | 0.750 | 0.375 |
| | Lubrication before compaction | | | |
| 13 | Magnesium stearate | 1.000 | 0.500 | 0.250 |
| | Lubrication after compaction | | | |
| 14 | Magnesium stearate | 1.000 | 0.500 | 0.250 |
| | Total weight of Portion A | 150.000 | 75.000 | 37.500 |
| | Portion B | | | |
| 15 | Microcrystalline cellulose | 98.000 | 49.00 | 24.500 |
| 16 | Croscarmellose sodium | 11.000 | 5.500 | 2.750 |
| 17 | Magnesium stearate | 1.000 | 0.500 | 0.250 |
| | Total weight of Portion B | 110.000 | 55.000 | 27.500 |
| 18 | Magnesium stearate | 2.000 | 1.000 | 0.500 |
| | Total weight Valsartan Layer(A + B) | 262.000 | 131.000 | 65.500 |
| | Total weight of Core Tablet (Valsartan Layer + Sacubitril Layer) | 462.000 | 231.000 | 115.500 |
| | Film Coating | | | |
| 19 | Opadry | 13.200 | — | — |
| 20 | Opadry | — | 6.600 | — |
| 21 | Opadry | — | — | 3.300 |
| 22 | Magnesium stearate | 1.000 | 0.500 | 0.250 |
| 23 | Methylene chloride | q.s. | q.s. | q.s. |
| 24 | Isopropyl alcohol | q.s. | q.s. | q.s. |
| | Total weight of coated tablet | 476.200 | 238.100 | 119.050 |

Brief Manufacturing Process
1. The pre-sifted Sacubitril sodium, microcrystalline cellulose, croscarmellose sodium, colloidal silicon dioxide and opadry green lake were blended in a suitable blender.
2. The dry mixed ingredients of step 1 were lubricated with magnesium stearate to form a blend.
3. The blend obtained in step 2 was passed through roller compactor to obtain compact mass/ribbons which were then milled and passed through appropriate sieve to obtain granules.
4. The granules obtained in step 3 were blended with microcrystalline cellulose, croscarmellose sodium and magnesium stearate to form a final blend.
5. The pre-sifted valsartan disodium, microcrystalline cellulose, croscarmellose sodium and colloidal silicon dioxide were blended in a suitable blender to form a dry mix.
6. The dry mixed ingredients of step 5 were lubricated with magnesium stearate to form a blend.
7. The blend obtained in step 6 was passed through roller compactor to obtain compact mass/ribbons which were milled and then sieved to obtain granules.
8. The granules of step 7 were lubricated with magnesium stearate.
9. The pre-sifted excipients of portion B were blended in a suitable blender to form a blend.
10. The blend obtained in step 9 was passed through roller compactor to obtain compact mass/ribbons which were then milled and passed through appropriate sieve to obtain granules.
11. The granules obtained in step 8 and 10 were mixed and then lubricated using magnesium stearate in a suitable blender to form a final blend.
12. The blends of steps 4 and 11 were compressed using suitable tooling to form a bilayer tablet which is further coated using Opadry and magnesium stearate.

Example 8

| S. No. | Ingredient | Qty/Tab. (mg) | | |
|---|---|---|---|---|
| | | 97/103 | 49/51 | 24/26 |
| | Sacubitril Layer | | | |
| 1 | Sacubitril Sodium eq. to Sacubitril | 97.200 | 48.600 | 24.300 |
| 2 | Microcrystalline cellulose | 59.746 | 29.873 | 14.936 |
| 3 | Croscarmellose sodium | 9.000 | 4.500 | 2.250 |
| 4 | Colloidal silicon dioxide | 2.000 | 1.000 | 0.500 |
| 5 | Opadry Lake blend Green | 0.054 | 0.027 | 0.014 |
| | Lubrication before compaction | | | |
| 6 | Magnesium stearate | 1.000 | 0.500 | 0.250 |
| | Lubrication after compaction | | | |
| 7 | Croscarmellose sodium | 9.000 | 4.500 | 2.250 |
| 8 | Microcrystalline cellulose | 19.000 | 9.500 | 4.750 |
| 9 | Magnesium stearate | 3.000 | 1.500 | 0.750 |
| | Total weight of Sacubitril layer | 200.000 | 100.000 | 50.000 |
| | Valsartan Layer Portion A | | | |
| 9 | Valsartan disodium eq. to Valsartan | 102.800 | 51.400 | 25.700 |
| 10 | Microcrystalline cellulose | 36.200 | 18.100 | 9.050 |
| 11 | Croscarmellose Sodium | 7.500 | 3.750 | 1.875 |
| 12 | Colloidal silicon dioxide | 1.500 | 0.750 | 0.375 |
| | Lubrication before compaction | | | |
| 13 | Magnesium stearate | 1.000 | 0.500 | 0.250 |
| | Lubrication after compaction | | | |
| 14 | Magnesium stearate | 1.000 | 0.500 | 0.250 |
| | Total weight of Portion A | 150.000 | 75.000 | 37.500 |
| | Portion B | | | |
| 15 | Microcrystalline cellulose | 70.950 | 35.475 | 17.737 |
| 16 | Pregelatinized starch | 33.000 | 16.500 | 8.250 |
| 17 | Colloidal silicon dioxide | 5.500 | 2.750 | 1.375 |
| 18 | Magnesium stearate | 0.550 | 0.275 | 0.138 |
| | Total weight of Portion B | 110.000 | 55.000 | 27.500 |
| 19 | Magnesium stearate | 2.000 | 1.000 | 0.500 |
| | Total weight Valsartan Layer(A + B) | 262.000 | 131.000 | 65.500 |
| | Total weight of Core Tablet (Valsartan Layer + Sacubitril Layer) | 462.000 | 231.000 | 115.500 |
| | Film Coating | | | |
| 20 | Opadry | 13.200 | — | — |
| 21 | Opadry | — | 6.600 | — |
| 22 | Opadry | — | — | 3.300 |
| 23 | Magnesium stearate | 1.000 | 0.500 | 0.250 |
| 24 | Methylene chloride | q.s. | q.s. | q.s. |
| 25 | Isopropyl alcohol | q.s. | q.s. | q.s. |
| | Total weight of coated tablet | 476.200 | 238.100 | 119.050 |

The composition of Example 8 can be prepared by the same process as given above for Example 7.

Example 9

| S. No. | Ingredient | Qty/Tab. (mg) 97/103 | 49/51 | 24/26 |
|---|---|---|---|---|
| | Sacubitril Layer (Portion A) | | | |
| 1 | Sacubitril Sodium eq. to Sacubitril | 97.200 | 48.600 | 24.300 |
| 2 | Microcrystalline Cellulose | 59.746 | 29.873 | 14.936 |
| 3 | Croscarmellose Sodium | 9.000 | 4.500 | 2.250 |
| 4 | Colloidal Silicon Dioxide | 2.000 | 1.000 | 0.500 |
| 5 | Opadry Lake blend Green | 0.054 | 0.027 | 0.014 |
| | Lubrication before compaction | | | |
| 6 | Magnesium Stearate | 1.000 | 0.500 | 0.250 |
| | Lubrication after compaction | | | |
| 7 | Croscarmellose Sodium | 9.000 | 4.500 | 2.250 |
| 8 | Microcrystalline Cellulose | 19.000 | 9.500 | 4.750 |
| 9 | Magnesium Stearate | 3.000 | 1.500 | 0.750 |
| | Total weight of Portion A | 200.000 | 100.000 | 50.000 |
| | Portion B | | | |
| 10 | Microcrystalline Cellulose | 26.727 | 13.363 | 6.682 |
| 11 | Croscarmellose Sodium | 3.000 | 1.500 | 0.750 |
| 12 | Magnesium Stearate | 0.273 | 0.137 | 0.068 |
| | Total weight of Portion B | 30.000 | 15.000 | 7.500 |
| | Total weight Sacubitril Layer(A + B) | 230.000 | 115.000 | 57.500 |
| | Valsartan Layer (Portion A) | | | |
| 13 | Valsartan Disodium eq. to Valsartan | 102.800 | 51.400 | 25.700 |
| 14 | Microcrystalline Cellulose | 36.200 | 18.100 | 9.050 |
| 15 | Croscarmellose Sodium | 7.500 | 3.750 | 1.875 |
| 16 | Colloidal Silicon Dioxide | 1.500 | 0.750 | 0.375 |
| | Lubrication before compaction | | | |
| 17 | Magnesium Stearate | 1.000 | 0.500 | 0.250 |
| | Lubrication after compaction | | | |
| 18 | Magnesium Stearate | 1.000 | 0.500 | 0.250 |
| | Total weight of Portion A | 150.000 | 75.000 | 37.500 |
| | (Portion B) | | | |
| 19 | Microcrystalline Cellulose | 62.364 | 31.182 | 15.591 |
| 20 | Croscarmellose Sodium | 7.000 | 3.500 | 1.750 |
| 21 | Magnesium Stearate | 0.636 | 0.318 | 0.159 |
| | Total weight of Portion B | 70.000 | 35.000 | 17.500 |
| 22 | Magnesium Stearate | 2.000 | 1.000 | 0.500 |
| | Total weight Valsartan Layer(A + B) | 222.000 | 111.000 | 55.500 |
| | Total weight of Core Tablet (Valsartan Layer + Sacubitril Layer) | 452.000 | 226.000 | 113.000 |
| | Film Coating | | | |
| 23 | Opadry | 13.560 | — | — |
| 24 | Opadry | — | 6.780 | — |
| 25 | Opadry | — | — | 3.390 |
| 26 | Magnesium Stearate | 1.000 | 0.500 | 0.250 |
| 27 | Methylene Chloride | q.s. | q.s. | q.s. |
| 28 | Isopropyl Alcohol | q.s. | q.s. | q.s. |
| | Total weight of coated tablet | 466.560 | 233.280 | 116.640 |

Brief Manufacturing Process

1. The pre-sifted sacubitril sodium, microcrystalline cellulose, croscarmellose sodium, colloidal silicon dioxide and opadry green lake were blended in a suitable blender.
2. The dry mixed ingredients of step 1 were lubricated with magnesium stearate to form a blend.
3. The blend obtained in step 2 was passed through roller compactor to obtain compact mass/ribbons which were then milled and passed through appropriate sieve to obtain granules.
4. The granules obtained in step 3 were blended with microcrystalline cellulose and croscarmellose sodium and then lubricated using magnesium stearate to form lubricated granules.
5. The pre-sifted microcrystalline cellulose, croscarmellose sodium and magnesium stearate were blended in a suitable blender to form a blend.
6. The blend obtained in step 5 was passed through roller compactor to obtain compact mass/ribbons which were then milled and passed through appropriate sieve to obtain granules.
7. The granules obtained in step 4 and 6 were mixed to form a final blend.
8. The pre-sifted valsartan disodium, microcrystalline cellulose, croscarmellose sodium and colloidal silicon dioxide were blended in a suitable blender to form a dry mix.
9. The dry mixed ingredients of step 8 were lubricated with magnesium stearate to form a blend.
10. The blend obtained in step 9 was passed through roller compactor to obtain compact mass/ribbons which were milled and then sieved to obtain granules.
11. The granules obtained in step 10 were lubricated with magnesium stearate.
12. The pre-sifted microcrystalline cellulose, croscarmellose sodium and magnesium stearate were blended in a suitable blender to form a blend.
13. The blend obtained in step 12 was passed through roller compactor to obtain compact mass/ribbons which were then milled and passed through appropriate sieve to obtain granules.
14. The granules obtained in step 11 and 13 were mixed and then lubricated using magnesium stearate to form a final blend.
15. The final blends of step 7 and 14 were compressed using suitable tooling to form a bilayer tablet which is further coated using Opadry, suitable solvents and magnesium stearate.

Dissolution Studies

Drug dissolution studies of the pharmaceutical compositions of Examples 3-6 were carried out in 900 mL of dissolution medium (pH 6.8 phosphate buffer) using USP dissolution apparatus II (Paddle) at 50 rpm and at temperature of 37°±0.5° C. Results are shown in Tables 1 and 2.

TABLE 1

Percentage drug (Sacubitril) release

| Time (min) | Percent drug release (Sacubitril) | | | | |
|---|---|---|---|---|---|
| | Example 3 | Example 4 | Example 5 | Example 6 | Entresto ® |
| 5.0 | 7.0 | 23.0 | 27.0 | 28.0 | — |
| 10.0 | 49.0 | 60.0 | 61.0 | 63.0 | 52.0 |
| 15.0 | 80.0 | 85.0 | 84.0 | 87.0 | 71.0 |
| 20.0 | 98.0 | 98.0 | 93.0 | 98.0 | 89.0 |
| 30.0 | 102.0 | 101.0 | 94.0 | 99.0 | 100.0 |

TABLE 2

Percentage drug (Valsartan) release

| Time (min) | Percent drug release (Valsartan) | | | | |
|---|---|---|---|---|---|
| | Example 3 | Example 4 | Example 5 | Example 6 | Entresto ® |
| 5.0 | 24.0 | 30.0 | 27.0 | 29.0 | — |
| 10.0 | 58.0 | 63.0 | 61.0 | 63.0 | 53.0 |
| 15.0 | 81.0 | 85.0 | 83.0 | 87.0 | 71.0 |
| 20.0 | 95.0 | 96.0 | 93.0 | 98.0 | 89.0 |
| 30.0 | 95.0 | 96.0 | 93.0 | 98.0 | 100.0 |

The above data reflects that the pharmaceutical compositions of the present invention are bioequivalent to the commercial available product Entresto®.

Stability Studies

The pharmaceutical composition of Example 3 was subjected to stability studies at 40° C./75% RH and the composition was found to be stable as shown below in table 3.

TABLE 3

Percentage drug assay

| % Assay | Initial | 2 Months | 3 Months |
|---|---|---|---|
| Sacubitril | 98.16 | 100.60 | 101.2 |
| Valsartan | 98.88 | 97.75 | 99.55 |

While the invention has been described in terms of its specific embodiments, certain modifications and equivalents will be apparent to those skilled in the art and are intended to be included within the scope of the invention.

We claim:

1. A pharmaceutical composition comprising:
   (1) a first component which comprises:
   (a) a first portion, wherein said first portion comprises sacubitril or its pharmaceutically acceptable salts, with one or more pharmaceutically acceptable excipients;
   (b) optionally a second portion, wherein said second portion comprises one or more pharmaceutically acceptable excipients; and
   (2) a second component which comprises:
   (a) a first portion, wherein said first portion comprises valsartan or its pharmaceutically acceptable salts, with one or more pharmaceutically acceptable excipients;
   (b) optionally a second portion, wherein said second portion comprises one or more pharmaceutically acceptable excipients,
   wherein:
   the first portion of the first component is in form of granules;
   the composition is stable at 40° C. and 75% relative humidity for 3 months; and
   the composition releases more than 85% of sacubitril or its pharmaceutically acceptable salts and valsartan or its pharmaceutically acceptable salts within 30 minutes.

2. The pharmaceutical composition according to claim 1, wherein valsartan is present in form of disodium salt.

3. The pharmaceutical composition according to claim 1, wherein valsartan is present in amorphous or crystalline form.

4. The pharmaceutical composition according to claim 1, wherein sacubitril is present in form of mono sodium salt.

5. The pharmaceutical composition according to claim 1, wherein sacubitril is present in amorphous or crystalline form.

6. The pharmaceutical composition according to claim 1, wherein the second component is in the form of powder, slugs, compacts, granules, beads, pellets, or minitablets.

7. The pharmaceutical composition according to claim 1, wherein the first and second components are present in single/mono layer.

8. The pharmaceutical composition according to claim 1, wherein the first and second components are present in separate layers.

9. The pharmaceutical composition according to claim 1, wherein the pharmaceutical composition is in the form of a tablet.

10. The pharmaceutical composition according to claim 1, wherein the pharmaceutical composition is further film coated using coating comprising film forming polymer and one or more pharmaceutically acceptable excipients.

11. The pharmaceutical composition according to claim 10, wherein the film coating comprises magnesium stearate.

12. The pharmaceutical composition according to claim 1, wherein the total weight of first component is about 100 mg to about 400 mg.

13. The pharmaceutical composition according to claim 1, wherein the total weight of second component is about 100 mg to about 400 mg.

14. A method for the treatment of heart failure in a patient comprising administering to the patient a pharmaceutical composition according to claim 1.

15. The pharmaceutical composition according to claim 1, wherein said pharmaceutical composition is prepared by a process of wet granulation, dry granulation, or direct compression.

16. The pharmaceutical composition according to claim 1, wherein said pharmaceutical composition is formed with a compression force ranging from 2 to 30 kN.

17. The pharmaceutical composition according to claim 1, wherein the pharmaceutically acceptable excipients are selected from the group comprising of one or more of filler/diluent, binder, disintegrant, lubricant, plasticizer, pH adjusting agent, pigment, opacifier, surfactant, glidant and/or combinations thereof.

* * * * *